(12) United States Patent
Sliski et al.

(10) Patent No.: US 6,285,735 B1
(45) Date of Patent: Sep. 4, 2001

(54) APPARATUS FOR LOCAL RADIATION THERAPY

(75) Inventors: Alan P. Sliski, Lincoln; Kenneth J. Harte, Carlisle, both of MA (US)

(73) Assignee: Photoelectron Corporation, Lexington, MA (US)

( * ) Notice: Subject to any disclaimer, the term of this patent is extended or adjusted under 35 U.S.C. 154(b) by 0 days.

(21) Appl. No.: 09/505,413

(22) Filed: Feb. 11, 2000

(51) Int. Cl.$^7$ .................................................. A61N 5/10
(52) U.S. Cl. ............................................ 378/65; 378/68
(58) Field of Search ................... 378/65, 64, 68, 378/193, 195, 196, 204, 205, 208

(56) References Cited

U.S. PATENT DOCUMENTS

| | | |
|---|---|---|
| 2,649,549 * | 8/1953 | Green ........................................ 378/65 |
| 3,752,990 | 8/1973 | Fischer . |
| 4,646,338 | 2/1987 | Skillicorn . |
| 4,694,480 | 9/1987 | Skillicorn . |
| 5,037,374 * | 8/1991 | Carol ................... 378/65 X |
| 5,090,043 | 2/1992 | Parker et al. . |
| 5,153,900 | 10/1992 | Nomikos et al. . |
| 5,165,093 | 11/1992 | Miller et al. . |
| 5,621,780 | 4/1997 | Smith et al. . |
| 5,748,699 | 5/1998 | Smith . |
| 6,181,770 * | 1/2001 | Ciravolo et al. ................ 378/117 |

* cited by examiner

Primary Examiner—David P. Porta
(74) Attorney, Agent, or Firm—McDermott, Will & Emery (57) ABSTRACT

A radiation applicator system is structured to be mounted to a radiation source for providing a predefined dose of radiation for treating a localized volume of tissue, such as the tissue surrounding the site of an excised tumor. The applicator system includes an applicator and, in some embodiments, an adapter. The adapter is formed for fixedly securing the applicator to a radiation source, such as a radiosurgery system which produces a predefined radiation dose profile with respect to a predefined location along its radiation producing probe. The applicator includes a shank and an end cap, wherein the end cap includes a substantially flat or convex treatment surface and is located at a distal end of the applicator shank. A proximate end of the applicator shank couples to the adapter. A distal end of the shank includes the end cap, which is adapted for engaging and preferably supporting the area to be treated with a predefined does of radiation. The applicator can include a low energy radiation filter inside of the applicator end cap to reduce undesirable low energy radiation emissions. A plurality of applicators having end caps of different sizes and shapes can be provided to accommodate treatment sites of various sizes and shapes. And, an adaptable applicator having a plurality of radiation positions can be provided to deliver a substantially cylindrical dose of radiation.

18 Claims, 7 Drawing Sheets

APPARATUS FOR LOCAL RADIATION THERAPY

BACKGROUND OF THE INVENTION

This invention relates to a miniaturized, programmable radiation source for use in delivering substantially constant or intermittent levels of x-rays to a specified region and, more particularly, to an apparatus for delivering a controlled dose of radiation to a localized volume of tissue, such as a volume of tissue of the human body.

In the field of medicine, radiation is used for diagnostic, therapeutic and palliative treatment of patients. The conventional medical radiation sources used for these treatments include large fixed position machines such as linear accelerators ("LINACs"), smaller transportable radiation delivery machines such as high-dose-rate after loaders, and catheters for low-dose-rate brachytherapy. The current state of the art treatment systems utilize computers to generate complex treatment plans for treating complex geometric volumes.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

Conventional radiation treatment systems, such as the LINAC used for medical treatment, utilize a high power remote radiation source and direct a beam of radiation at a target volume, such as a tumor inside the body of a patient. This type of treatment is referred to as teletherapy because the radiation source is located a predefined distance, typically on the order of one meter, from the target. This treatment suffers from the disadvantage that tissue disposed between the radiation source and the target is exposed to radiation.

An alternative treatment system utilizing a point source of radiation is disclosed in U.S. Pat. No. 5,153,900 issued to Nomikos et al., owned by the assignee of the present application, which is hereby incorporated by reference. The system includes a miniaturized, insertable probe capable of producing low power radiation in predefined dose geometries or profiles disposed about a predetermined location. One advantage of this system is that the radiation is applied to treat a predefined tissue volume, without significantly affecting the tissue in adjacent volumes.

A typical use of the described radiation therapy system involves positioning the insertable probe into the tumor or the site where the tumor or a portion of the tumor was removed to treat the tissue adjacent the site with radiation. In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, it is desirable that the insertable probe be adjustably supported in a compliant manner to accurately position the radiation source with respect to the treated site and accommodate normal minor movements of the patient, such as movements associated with breathing.

Accordingly, it is an object of the present invention to provide an improved system for delivering radiation to a localized region.

SUMMARY OF THE INVENTION

The present invention is directed to a radiation applicator system which is mountable to a radiation source in order to apply a predefined dose of radiation to a surface of a body to treat a volume of tissue. The radiation applicator system includes an applicator and, preferably, an adapter. When included, the adapter couples the applicator to a radiation source. The applicator includes an applicator shank and an applicator end cap. The adapter may take any of a variety of forms, and may, for example, be integral with the shank, the radiation source, or may include one or more separate components which couple the shank to the radiation source. The adapter may also be formed from some combination thereof. In the preferred form, the adapter is a separate component that engages the applicator shank at the shank's proximate end and thereby allows coupling of the applicator to the radiation source, when the adapter is coupled to the radiation source. At the opposite and distal end of the applicator shank is the applicator end cap, having a substantially flat or convex treatment surface for applying a predefined dose of radiation across a surface contour to treat a predefined volume of tissue surrounding a surgical site. Preferably, the applicator end cap and surface contour coincide such that the surface of the applicator end cap engages and supports the surface of the volume to be treated and applies a predetermined dose of radiation across the surface to that volume. In the preferred embodiment, the end cap includes a substantially conical void region which originates proximate to the distal end of the probe and increases in diameter as it approaches the treatment surface of the end cap. This conical void region helps to form the radiation beam into a column form.

In one embodiment, the radiation source includes an elongated probe and is adapted for producing a predefined radiation dose profile about a predetermined location with respect to the probe. In this embodiment, the applicator system can also include a low energy radiation filter adapted to surround at least a portion of the probe within the applicator end cap. The low energy radiation filter serves to reduce the low energy radiation produced by the probe which can damage tissue adjacent the applicator end cap. The applicator end cap engages the area to be treated, such as the area adjacent the site where a tumor was removed in order to permit the application of radiation to prevent the regrowth of the tumor.

Preferably, the applicator system is adapted to be mounted to the radiation source and encase the elongated probe to form a self contained treatment assembly. During a surgical procedure, the treatment assembly, including the applicator system and the radiation source, can be supported by a carrier system. The carrier system can be adapted to support the treatment assembly in a substantially weightless configuration in order to facilitate positioning by the physician during surgery and to accommodate substantially minor movements by the patient, such as breathing.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1A:
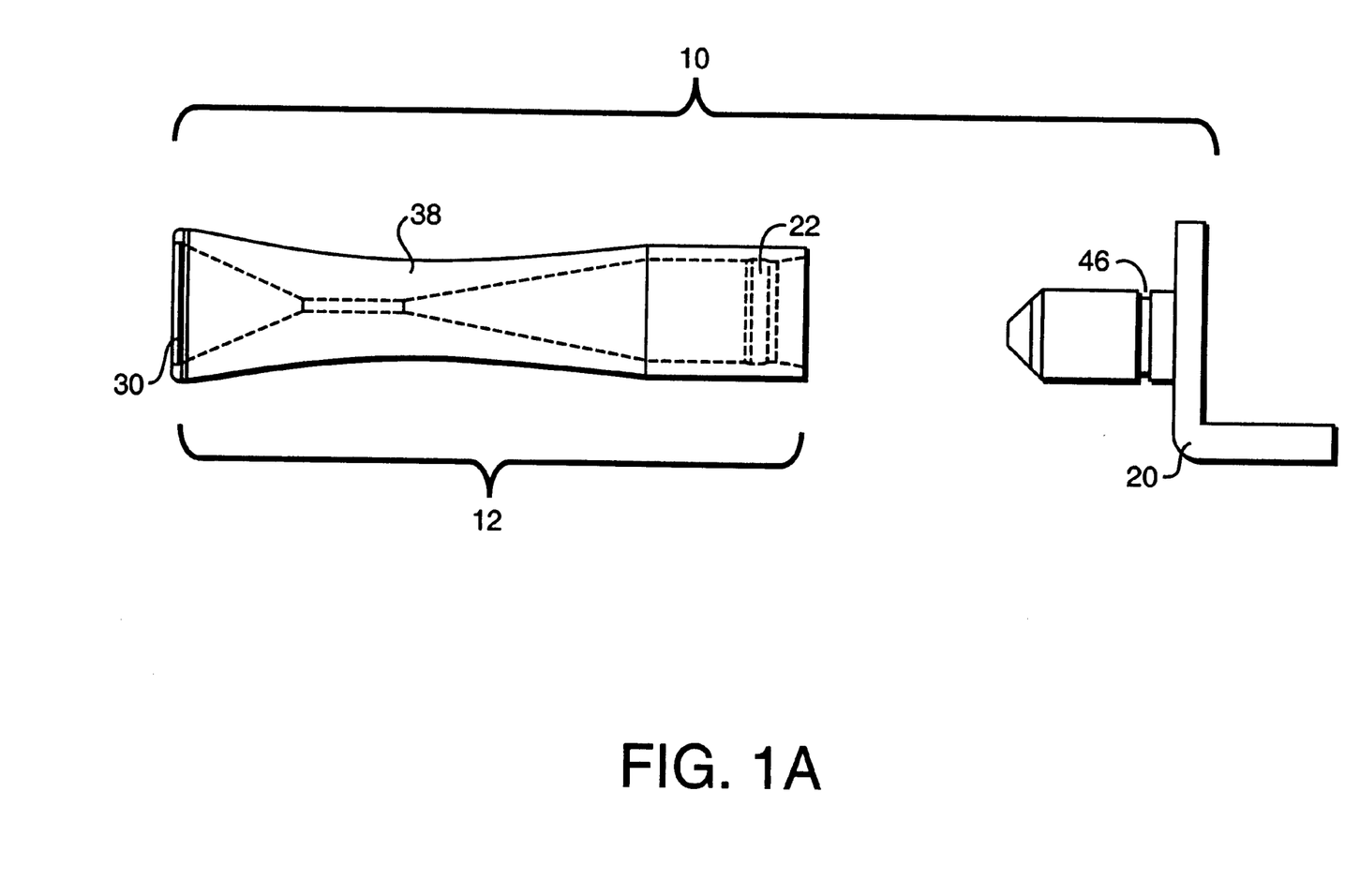
FIG. 1A is a diagrammatic exploded view of an applicator system, in accordance with the present invention.

FIG. 1A shows an applicator system 10 for applying a dose of radiation across a predefined contour of a body to treat a predefined volume of tissue. The applicator system 10 preferably includes an applicator 12 and an adapter 20, but in some embodiments the adapter may not be included. Applicator 12 includes a shank 38 and an end cap 30, wherein end cap 30 is located at a distal end of shank 38. A proximate end of shank 38 removably engages with adapter 20 to form applicator system 10. The preferred adapter 20 of FIG. 1A is structured for attaching applicator system 10 to a radiation source. At the opposite end of shank 38, applicator end cap 30 includes a substantially planar, or convex, treatment surface for engaging and conforming a tissue cavity to a desired shape in order to permit the volume of tissue adjacent to applicator end cap 30 to be treated with a predefined dose of radiation. In the preferred embodiment, the shank 38 includes a substantially conical void region which originates proximate to the distal end of the probe and increases in diameter as it approaches the treatment surface of the end cap. This conical void region helps to form the produced radiation beam into a truncated conical form. The shape of the distal surface of the applicator end cap 30 can also be selected to closely approximate the shape of the surface to be treated. The applicator system 10 can also include a low energy filter 34 (shown in FIG. 3B) for absorbing low energy radiation.

Figure 1B:
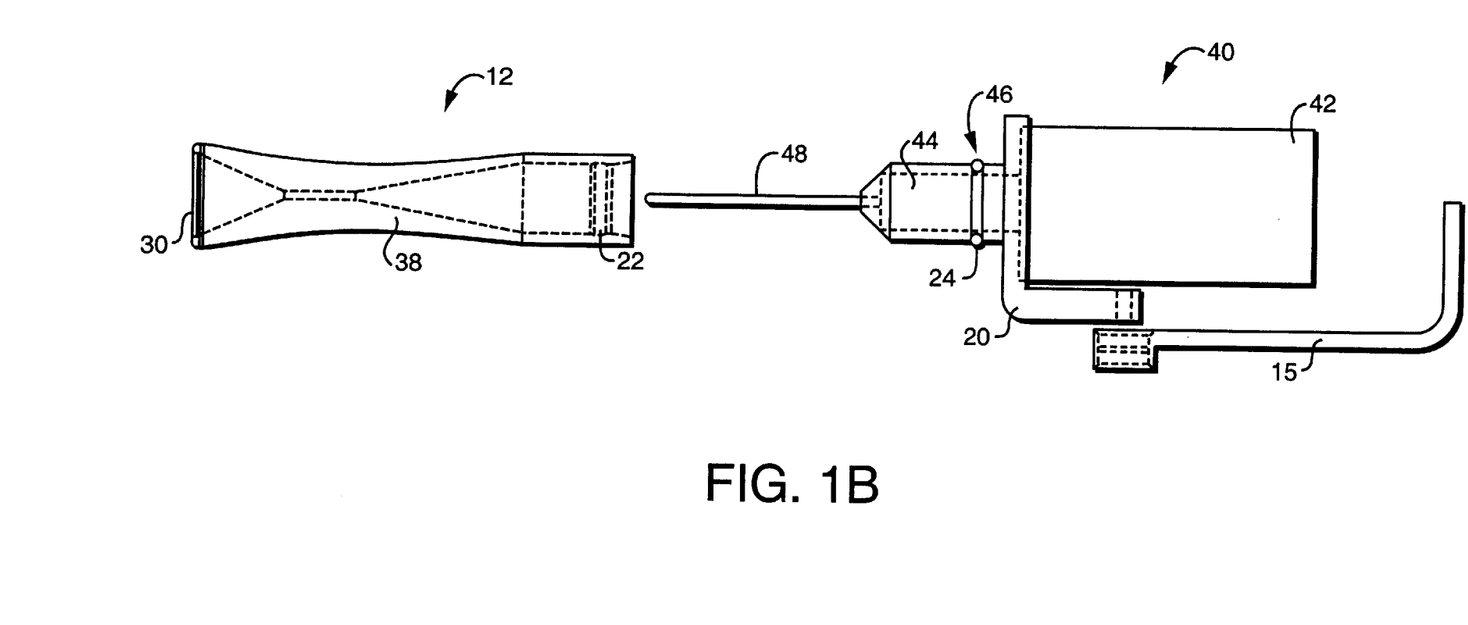
FIG. 1B is a diagrammatic exploded view of the applicator system of FIG. 1A and a prior art radiation source, with the applicator system adapter coupled to the radiation source.

FIG. 1B shows adapter 20 of applicator system 10 mounted on a radiation source, such as a radiosurgery system 40. The radiosurgery system 40 includes a housing 42, a barrel 44 and an elongated probe 48. The radiosurgery system 40 is adapted for generating a field of radiation having a predefined dose profile about the distal end of probe 48. The applicator system 10 is adapted to fit over probe 48 and barrel 44 of the radiosurgery system 40.

In FIG. 1B, adapter 20 is shown supported by a carrier support system arm 15, the carrier support system thereby supporting the radiosurgery system. The adapter includes a circumferential groove 46 and a retaining spring 24 (or O-ring) mounted in groove 46. A portion of spring 24 extends above the surface of the adapter 44 to facilitate engagement of applicator 12 to adapter 20. The proximate end of the applicator shank 38 is adapted to fit over adapter 20 and includes an interior, circumferential groove 22 which is adapted to receive the portion of the spring 24 that extends above the adapter groove 46.

Figure 2A:
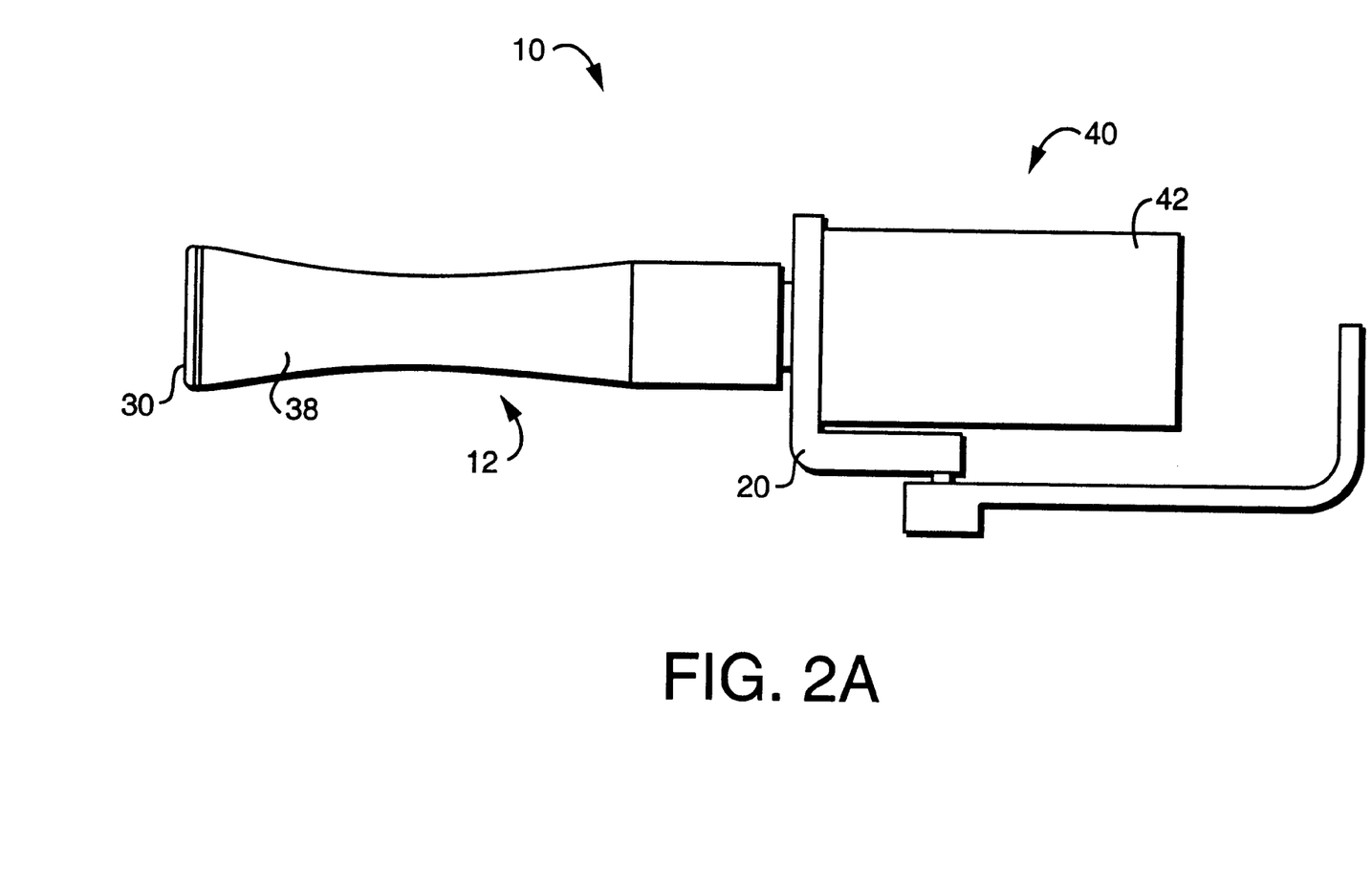
FIG. 2A is a diagrammatic view of the applicator system and radiation source of FIG. 1B in assembled form.
Figure 2B:
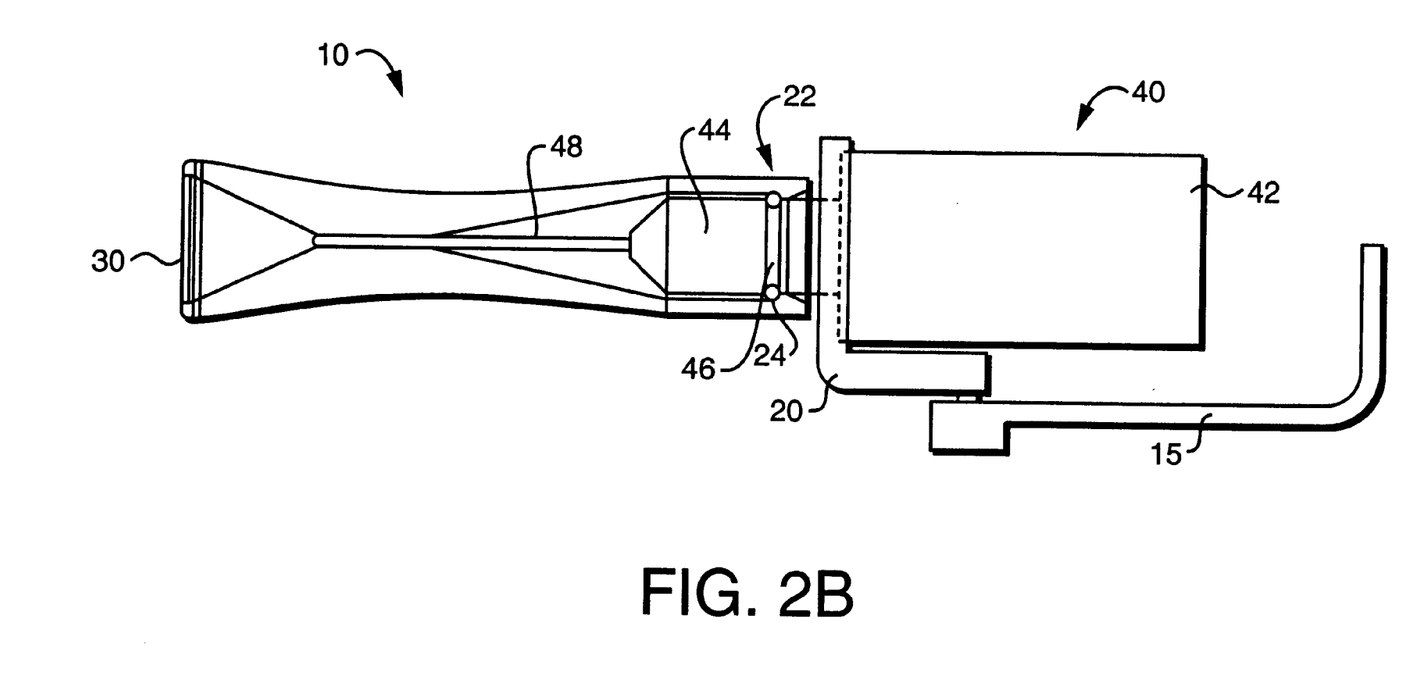
FIG. 2B is a diagrammatic cross-sectional view of the applicator system mounted to the radiation source of FIG. 2A.

As shown in FIGS. 2A and 2B, the applicator 12 slidably fits over and couples to adapter 20, which is secured to radiosurgery system 40. When applicator 12 is slid on to adapter 20, spring 24 is compressed by the interior surface of shank 38 and, once groove 22 aligns with spring 24, the spring expands to fill groove 22, thereby securely coupling shank 38 of applicator 12 to adapter 20. Consequently, applicator 12 is secured over probe 48 of the radiosurgery system 40. As a person having ordinary skill will appreciate, other well known coupling methods and mechanisms can be used, for example: a bayonet coupling, a threaded coupling, spring loaded ball bearings and detents, and set screws.

In the preferred embodiment (shown in FIG. 3A), the applicator end cap 30 is attached to a recess in the distal end of the applicator shank 38 by means of a biocompatible epoxy (such as Epo-Tek 353-ND available from Epo-Tek of Billerica, Mass.). Alternatively, end cap 30 may be either integral with shank 38 to form a unitary applicator or may be in the form of a detachable cap which fits over the distal end of the applicator shank 38 (shown in FIG. 3B). In another alternative embodiment, also shown in FIG. 3B, the applicator shank 38 includes an applicator barrel 32 which supports a shank extension 38'. End cap 30, in any of its aforementioned embodiments, is then attached to the shank extension 38'.

Figure 3A:
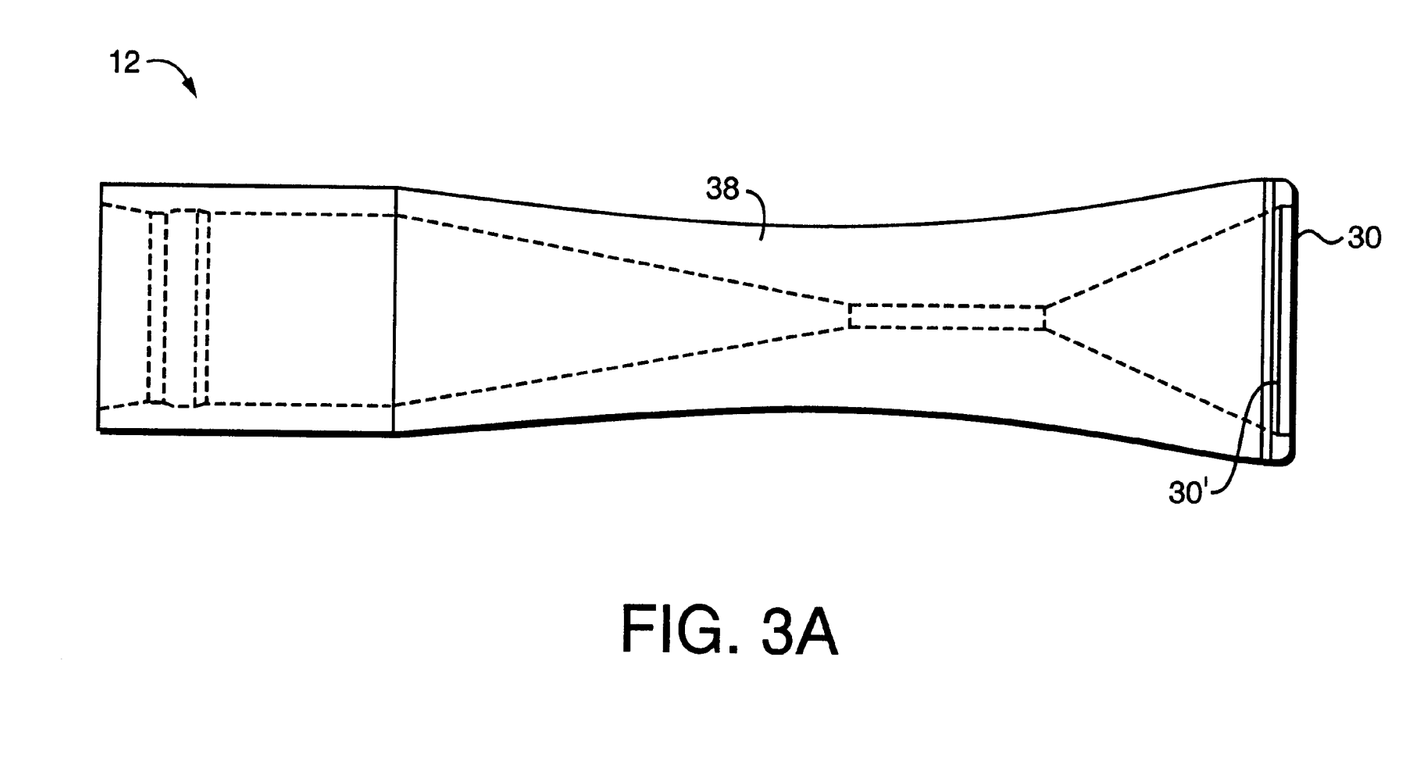
FIG. 3A is a diagrammatic cross sectional view of the applicator portion of the applicator system of FIG. 2B.
Figure 3B:
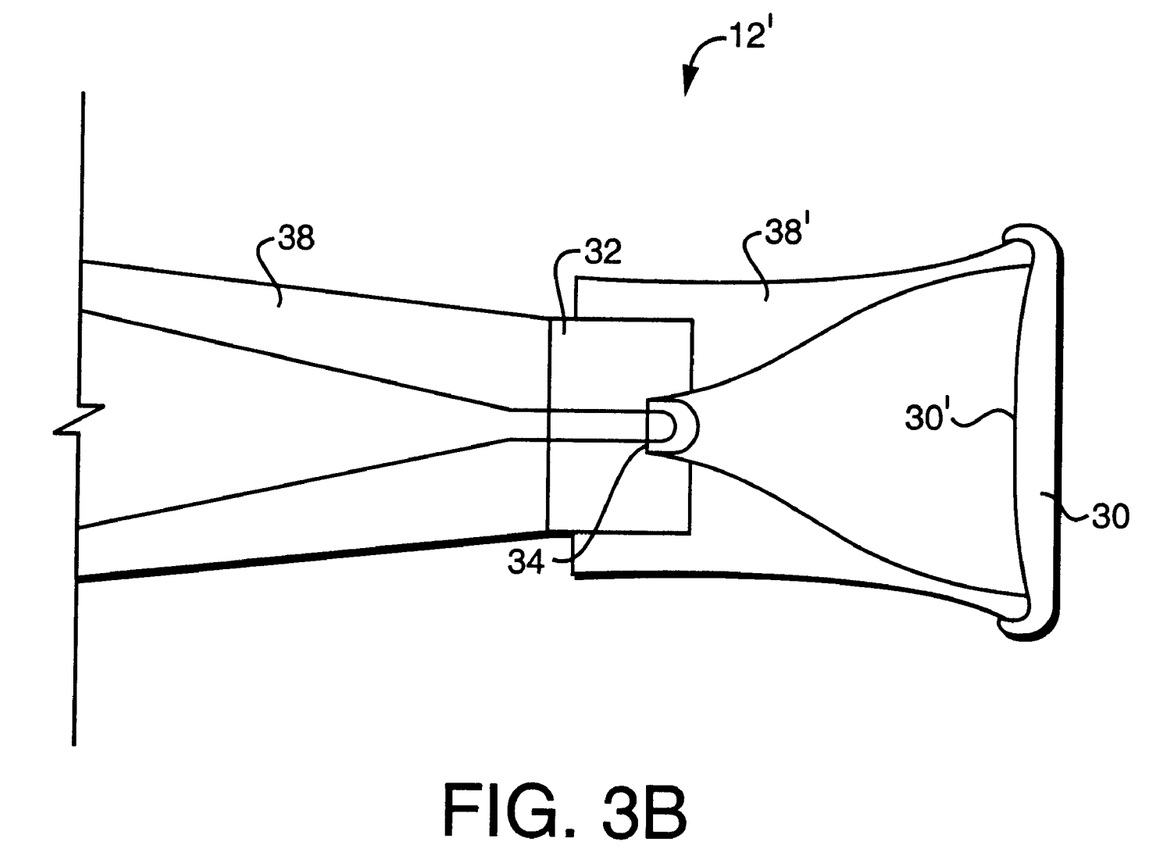
FIG. 3B is a diagrammatic cross sectional view of an alternative form of an applicator, in accordance with the present invention.

The applicator 12 or 12' may further include a low energy radiation filter 34 that is formed from a material such as aluminum, that absorbs or blocks low energy radiation produced by the probe 48 in order to prevent adverse effects on tissue adjacent the applicator end cap 30. The shape of the low energy filter 34 is determined by the output profile of the radiation source in the radiation probe 48 and is preferably hemispherical. Preferably, the thickness of the low energy filter 34 is selected to reduce the low energy radiation produced outside the applicator end cap 30 to an acceptable level for the required treatment.

In either embodiment, end cap 30 is provided with a substantially planar treatment surface which is adapted to engage and support the surface area of a volume of tissue to be treated. Alternatively, the treatment surface of the applicator end cap 30 can be convex or provided with a pre-defined surface contour in order to facilitate the application of radiation to a surface area desired treatment volume. The contour of the inner surface 30' of end cap 30 is formed to allow the system to deliver a predetermined radiation pattern, such as a flat field of radiation adjacent the outer surface in order to treat uniformly over the surface. The shape of the field can be substantially predefined or "flattened" by predefining the thickness, density and contour of the end cap 30 in order to filter the radiation and modify the dose profile.

Preferably, the applicator shank 38, shank extension 38' and barrel 32 (in FIG. 3B) of the applicator 12' are formed (e.g., either molded or machined) from a lead filled crystal, such as ClearPB from Atlantic Nuclear Inc. of Canton, Mass. Filter 34 can be fixed in place using a biocompatible epoxy (such as Epo-Tek 353-ND). Applicator end cap 30 is preferably formed from a biocompatible acrylic, available from Cyro Industries of Rockaway, N.J. Preferably, the applicator end cap 30 is formed (such as by molding or machining) from a single piece of acrylic and fixed in place within shank 38 or shank extension 38' using the biocompatible epoxy. The applicator end cap forms an interior conical void region which aids in forming the beam in a predefined shape, such as a column. In the embodiment of FIG. 3B shank extension 38' includes one or more internal ridges which are adapted to engage one or more ridges on the outer surface of the barrel 32 in order to retain the shank extension 38' and end cap 30 in position with respect to barrel 32. Alternatively, the shank extension 38' can be fastened to barrel 32 by any acceptable method, such as via epoxy. Preferably, the low energy filter is formed from an aluminum material and the radiosurgery system 40 is a photon-radiosurgery system (PRS) available from Photoelectron Corp. of Lexington, Mass.

Figure 4:
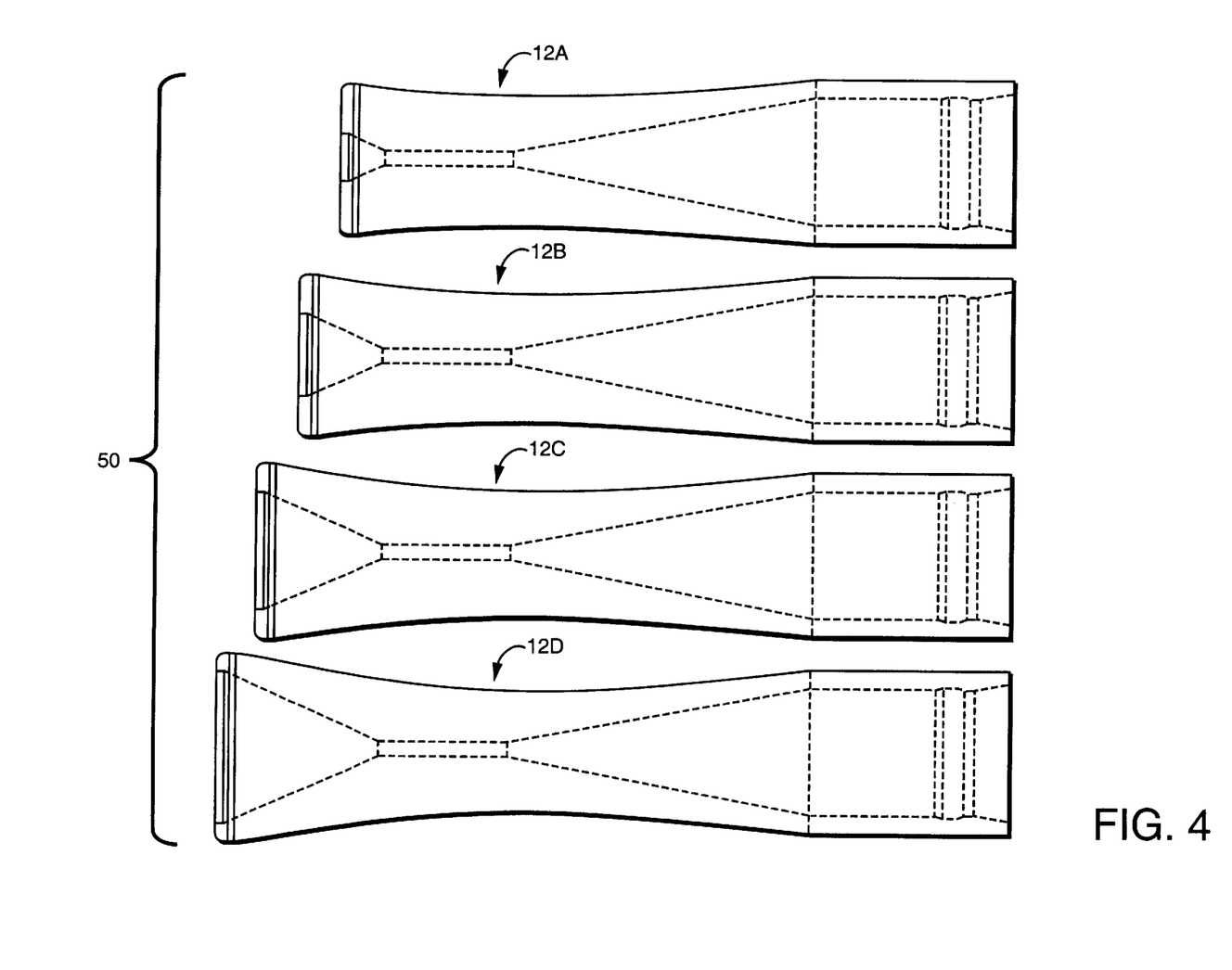
FIG. 4 is a diagrammatic cross sectional view of a plurality of applicators, as part of a kit, in accordance with another aspect of the invention.

FIG. 4 shows an example of a kit 50 containing a plurality of applicators 12A–12D of the form shown in FIG. 3A, the kit also preferably includes an accompanying plurality of adapters 20 (not shown). In kit 50, applicators 12A–12D include circular shaped surface applicators of differing size. But more generally, each applicator can include a different size and/or cross-sectioned shaped applicator end cap, as may be used to treat different sites. Those skilled in the art will appreciate that applicators having a end cap of different shape and size to that shown in FIG. 4 may also be used, primarily as a function of any of a variety of considerations, such as the shape and size of the site to be radiated and/or the predetermined desired radiation pattern and dose to be delivered. A kit may also be formed using applicators of the type shown in FIG. 3B. Alternatively, a kit may also include a single shank 38 and a plurality of detachable end caps 30.

Preferably, during treatment, the radiosurgery system 40 with the attached applicator adapter 10 is supported by the gimbal mounted support system such as that disclosed in commonly owned U.S. patent application Ser. No. 09/502,473, which is hereby incorporated by reference. This allows a physician applying treatment to guide the tip of the applicator without having to support the weight of the device for the duration of the treatment. An example of such a system is the carrier support system shown in part in FIGS. 1B, 2A and 2B.

The above described system can be used to treat the site where a tumor or a portion of a tumor was removed with a predefined dose of radiation. The treatment involves inserting the applicator end cap into the site and delivering a continuous or intermittent dose of radiation to the tissue adjacent the exterior surface of the applicator end cap. Preferably, the shape of the applicator end cap is selected to closely match the shape of the excised tumor in order to support the surrounding tissue and provide accurate application of the radiation dose.

The invention may be embodied in other specific forms without departing from the spirit or essential characteristics thereof. For example, the adapter of the applicator system could be integral with, or part of, the radiation source. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A radiation applicator system for use with a radiation source for facilitating the application of a dose of radiation to a volume, said radiation applicator system comprising:
   A) an applicator, adapted to substantially encase a radiating probe of said radiation source, said applicator including:
      i) a shank having a proximate end and a distal end; and
      ii) an end cap secured to said shank distal end and defining a substantially planar or convex treatment surface adapted to engage said area to receive said dose of radiation.

2. A radiation applicator system according to claim 1 wherein said radiation source probe is an elongated probe extending from said housing and adapted for producing predefined doses of radiation at a distal end of said probe; and
   said end cap is adapted to receive said distal end of said probe, whereby radiation produced by said probe can be applied to said area defined by said surface of said end cap.

3. A radiation applicator system according to claim 1 wherein said end cap defines an interior void region adapted to receive and encase at least a portion of said probe distal end and to facilitate formation of a radiation beam corresponding to said dose of radiation.

4. A radiation applicator system according to claim 3 wherein said void region is substantially conical in shape and extends in an increasing diameter from about said probe distal end to about said treatment surface.

5. A radiation applicator system according to claim 1 wherein said shank includes a fastening element adapted to fasten said radiation applicator at a first predefined position with respect to said radiation source.

6. A radiation applicator system according to claim 1 wherein said shank includes a fastening element adapted to fasten said radiation applicator in one of a plurality of positions with respect to said radiation source.

7. A radiation applicator system according to claim 1 wherein said shank includes:
   a base shank, having a proximate end and a distal end, wherein said base shank proximate end is the proximate end of said shank and said base shank distal end includes a third coupler; and
   a shank extension having a proximate end and a distal end, wherein said shank extension distal end is said shank distal end and said shank extension proximate end includes a fourth coupler suited for mated engagement with said third coupler.

8. A radiation applicator system according to claim 1 wherein the shank is comprised of a lead filled crystal material.

9. A radiation applicator system according to claim 1 wherein the end cap is comprised of an acrylic material.

10. A radiation applicator system according to claim 1 further comprising:
    B) an adapter, including:
       i) a first coupler suited for mated engagement with said shank proximate end, and
       ii) a second coupler suited for mated engagement with said radiation source.

11. A radiation applicator system according to claim 1 wherein said end cap is formed from a material having a predefined thickness at predefined locations.

12. A radiation applicator system according to claim 1 further comprising a low energy filter, coupled to said distal end of the applicator, and adapted to attenuate low energy radiation emitted from said radiating portion of said probe.

13. A radiation applicator system according to claim 1 wherein said end cap is removably secured to said shank.

14. A radiation applicator system for use with a radiation source for facilitating the application of a dose of radiation to a volume, said radiation applicator system comprising:
    A) an applicator, adapted to substantially encase an elongated radiating probe of said radiation source, said applicator including:

i) a shank having a proximate end and a distal end; and
ii) an end cap secured to said shank distal end and defining a substantially planar or convex treatment surface adapted to engage said area to receive said dose of radiation, wherein said radiating probe includes a radiating end and wherein said end cap defines an interior substantially conical void region adapted to receive and encase at least a portion of said probe radiating end and to facilitate formation of a radiation beam corresponding to said dose of radiation; and B) an adapter, including:
i) a first coupler suited for mated engagement with said shank proximate end, and
ii) a second coupler suited for mated engagement with said radiation source.

15. A kit for applying radiation to a volume, said kit comprising:
a radiation source adapted to produce a predefined radiation dose profile; and
a plurality of radiation applicator systems, each of said radiation applicator systems including:
A) an applicator, adapted to substantially encase a radiating probe of said radiation source, said applicator including:
i) a shank having a proximate end and a distal end; and
ii) an end cap secured to said shank distal end and defining a substantially planar or convex treatment surface adapted to engage said area to receive said dose of radiation.

16. A kit according to claim 15, said kit further comprising
B) an adapter, including:
i) a first coupler suited for mated engagement with said shank proximate end, and
ii) a second coupler suited for mated engagement with said radiation source.

17. A kit according to claim 15 wherein the end cap of at least one of the plurality of applicator systems is different in size or cross-sectional shape than the end cap of at least one of the other applicator systems from the plurality of applicator systems.

18. A kit according to claim 15 wherein at least one of said plurality of applicator systems has a shank which includes:
a base member, having a proximate end and a distal end, wherein said base member proximate end is the proximate end of said shank and said base shank distal end includes a third coupler; and
a shank extension having a proximate end and a distal end, wherein said shank extension distal end is said shank distal end and said shank extension proximate end includes a fourth coupler suited for mated engagement with said third coupler.

* * * * *